US012150898B2

United States Patent
Arba Mosquera et al.

(10) Patent No.: US 12,150,898 B2
(45) Date of Patent: Nov. 26, 2024

(54) METHOD FOR PREDICTING A FUTURE POSITION OF A TARGET POINT OF AN EYE TO COMPENSATE FOR A LATENCY OF AN IMAGE EVALUATION, CONTROL DEVICE AND TREATMENT APPARATUS

(71) Applicant: SCHWIND eye-tech-solutions GmbH, Kleinostheim (DE)

(72) Inventors: Samuel Arba Mosquera, Aschaffenburg (DE); Shwetabh Verma, Aschaffenburg (DE)

(73) Assignee: SCHWIND eye-tech-solutions GmbH, Kleinostheim (DE)

( * ) Notice: Subject to any disclaimer, the term of this patent is extended or adjusted under 35 U.S.C. 154(b) by 346 days.

(21) Appl. No.: 17/574,191

(22) Filed: Jan. 12, 2022

(65) Prior Publication Data

US 2022/0218525 A1    Jul. 14, 2022

(30) Foreign Application Priority Data

Jan. 14, 2021  (DE) ............... 10 2021 100 645.7

(51) Int. Cl.
*A61F 9/008* (2006.01)
*G06T 7/20* (2017.01)
*G06T 7/70* (2017.01)

(52) U.S. Cl.
CPC ........ *A61F 9/00814* (2013.01); *A61F 9/0084* (2013.01); *G06T 7/20* (2013.01);
(Continued)

(58) Field of Classification Search
CPC ...... A61F 9/00814; A61F 9/0084; G06T 7/70; G06T 7/20
(Continued)

(56) References Cited

U.S. PATENT DOCUMENTS 6,210,401 B1 * 4/2001 Lai .............. B23K 26/032
                                                606/4
2005/0273185 A1 * 12/2005 Teiwes ............ G06F 3/013
                                                702/187
(Continued)

FOREIGN PATENT DOCUMENTS

| DE | 10 2005 025 462 A1 | 2/2006 | |
|---|---|---|---|
| EP | 2497414 A1 * | 9/2012 | ............ A61B 3/102 |
| EP | 2 547 298 B1 | 5/2019 | |

OTHER PUBLICATIONS

Notification of the Second Office Action issued Jun. 21, 2024 in CN Appl. No. 202210038914.1.

*Primary Examiner* — Mohammad Ali
*Assistant Examiner* — Joshua T Sanders
(74) *Attorney, Agent, or Firm* — MEDLER FERRO WOODHOUSE & MILLS PLLC (57) ABSTRACT

A method is disclosed for determining a position of a target point of a human or animal eye during a medical treatment of the eye to allow an improved target accuracy for triggering a laser pulse to a respective target point. The method includes capturing a respective picture of the eye at a first point of time and a later second point of time, determining movement information with respect to a movement of the eye and/or of the target point based on the respective pictures and determining prediction data. The prediction data including a prediction for a future position and/or orientation of the target point at a later point of time, based on the movement information, wherein the later point of time is temporally spaced from the second point of time by a period of time, the duration of which is derived from a latency of an image evaluation.

13 Claims, 3 Drawing Sheets

(52) U.S. Cl.
CPC ...... *G06T 7/70* (2017.01); *A61F 2009/00872* (2013.01); *G06T 2207/30041* (2013.01)

(58) Field of Classification Search
USPC .......................................................... 700/59
See application file for complete search history.

(56) References Cited

U.S. PATENT DOCUMENTS

| 2008/0055543 | A1* | 3/2008 | Meyer | ..................... | A61B 3/102 |
| | | | | | 351/205 |
| 2019/0175281 | A1* | 6/2019 | Dishler | .................. | A61B 34/10 |

* cited by examiner

METHOD FOR PREDICTING A FUTURE POSITION OF A TARGET POINT OF AN EYE TO COMPENSATE FOR A LATENCY OF AN IMAGE EVALUATION, CONTROL DEVICE AND TREATMENT APPARATUS

FIELD

The invention relates to a method for determining a position of a target point of a human or animal eye, in particular of a cornea of the eye, during a medical treatment of the eye. A second aspect of the invention relates to a method for controlling an eye surgical laser of a treatment apparatus during a treatment of a cornea of a human or animal eye depending on a position and/or orientation of a target point of the eye. A third aspect of the invention relates to a control device. A further aspect of the present invention relates to a treatment apparatus. In addition, the invention also relates to a computer program as well as to a computer-readable medium.

BACKGROUND

Treatment apparatuses and methods for controlling eye surgical lasers for correcting an optical visual disorder and/or pathologically or unnaturally altered areas of a cornea of a patient are known in the prior art. Therein, a pulsed laser and a beam device can for example be formed such that laser pulses cause photodisruption and/or photoablation in a focus located within the organic tissue to remove tissue, in particular a tissue lenticule, from the cornea.

For achieving an optimum treatment result, it is required that the laser pulses get into a target point of the eye, in particular of the cornea of the eye, with an accuracy as high as possible. Therein, for an accuracy as high as possible, it is advantageous if the eye is, in particular continuously, captured by a capturing device. This can also be referred to as tracking. In other words, a movement of the eye can be tracked. The movement of the eye can then be used in determining the respective target point for the laser pulses.

From EP 1 923 026 B1, a system for ablating the cornea of an eye is known, wherein nominal targets are determined to each laser pulse before ablating the cornea of the eye. Based on the signals of an eye tracker received temporally delayed, the distribution of the laser pulses to actual target locations is calculated. In order to correct errors, further laser pulses with associated nominal target locations can then be defined.

SUMMARY

It is an object of the present invention to allow an improved target accuracy for triggering a laser pulse onto a respective target point.

According to the invention, this object is solved by the subject matters of the independent claims. Advantageous embodiments with convenient developments are the subject matter of the dependent claims.

A first aspect of the present invention is based on a method for determining a position of a target point of a human or animal eye, in particular of a cornea of the eye, during a medical treatment of the eye. According to the invention, the method comprises the following steps:

capturing a respective picture of the eye at least at a first point of time and a later second point of time, determining movement information with respect to a movement of the eye and/or of the target point based on the respective pictures, and determining prediction data, which includes a prediction for a future position and/or orientation of the target point at a later point of time, based on the movement information, wherein the later point of time is temporally spaced from the second point of time by a period of time, the duration of which is at least derived from a latency of an image evaluation.

The respective pictures of the eye can each be pictures, which are generated by an arbitrary, preferably imaging, capturing method. For example, the capturing method can be thermography, ultrasonic sensor technology or any other imaging method. Preferably, the pictures of the eye are respective camera images. In other words, respective camera images of the eye can be captured at least at the first point of time and the later second point of time. For example, this can be effected by a camera. In particular, the pictures or the camera images are respectively different frames of a moving image or of a video signal. In particular, the pictures are each a digital picture, thus for example an image file or a video file. In particular, a continuous video signal can be captured by a camera, wherein the respective pictures can be part of the video signal, in particular individual images or frames, of the video signal.

The picture, which is captured at the first point of time, can represent or image the eye and the cornea thereof, respectively, in the first point of time or at the first point of time. The picture, which is captured at the first point of time, is also referred to as the first picture in the following. The picture of the eye, which is captured at the second point of time, can represent or image the eye in or at the second point of time. The picture, which is captured at the second point of time, is also referred to as the second picture in the following. Therein, the second point of time is temporally after the first point of time. In other words, the second picture represents the eye at a later point of time than the first picture. In other words, the second picture can image the eye at a later point of time than the first picture. Therein, the present disclosure with two pictures at two different points of time is to be purely exemplarily understood. Of course, it is also possible to capture a respective picture at more than two points of time, thus in particular a respective picture at two, three, four, five, six, seven, eight etc. points of time. Analogously, it is possible to capture more than one picture at each of the points of time or at individual points of time. Thus, it can for example be provided that more than one picture of the eye is captured at the first point of time.

From the respective pictures, in particular the first picture and the second picture, the movement information with respect to the movement of the eye and/or of the target point can be determined. If, as previously described, more pictures of the eye than only the first and the second picture are captured, they can of course also be used for determining the movement information. For example, a relative movement of the eye and/or of the target point between the first and the second picture can be determined as the movement information. In case of multiple pictures, a respective relative movement between respective pictures can be determined as a part of the movement information. For example, the respective relative movement between two images captured at adjacent points of time can be captured or determined. The movement information or the relative movement can for example be determined and indicated, respectively, in the form of a respective vector (in case of a translational movement) and/or an angle (in case of a rotational movement). Therein, the movement information for different degrees of freedom, for instance for three independent translational degrees of freedom and/or three independent rotational degrees of freedom, can be determined in common and/or independently of each other. The acceleration and/or the speed or the respective values for the acceleration and/or the respective values for the speed can constitute the movement information or be part of the movement information.

Based on the movement information, the prediction for the future position and/or orientation of the target point at the later point of time can then be determined. This prediction can be determined as a part of the prediction data. Therein, the later point of time is temporally spaced from the second point of time by the period of time, the duration of which is at least derived from the latency of the image evaluation. In other words, the position and/or orientation of the target point at such a later point of time can be determined by the prediction, at which the determination of the prediction data is completed and/or the prediction data is output. Thus, the invention is based on the idea that in conventional determination of the position and/or orientation of the target point based on the respective pictures or based on the second picture at the second point of time, a position and/or orientation would be determined, which is already in the past at a point of time, at which the determination is completed, since the image evaluation is afflicted with latency. Therefore, an idea of the present invention is based on the fact to consider the latency in that the position and/or orientation of the eye are predicted for the later point of time. In this manner, the prediction data contains the predicted future position and/or orientation of the target point at the later point of time, at which the image evaluation, thus for example the capture of the respective pictures, the determination of the movement information and/or the determination of the prediction data, is already completed. Thus, the temporal latency of the image evaluation can be bridged by the prediction. Of course, it can be reasonable in the individual case to only consider the latency of selected or only a part of the method steps. In this case, it can for example be that the later point of time is closer to the second point of time compared to an embodiment, in which all of the steps are considered. Alternatively or additionally, it can of course be advantageous to consider other and/or additional method steps or other events in a determination of the period of time, by which the later point of time is in the future from the second point of time. For example, method steps afflicted with latency, subsequent to the determination of the position and/or orientation of the target point, can be considered. This will be explained in more detail later.

According to a development, it is provided that during the determination of the prediction data, the later point of time is at most temporally spaced as far as the first point of time. In other words, while the step of determining the prediction data is performed, the later point of time can be in the future at most by the same period of time, by which period of time the first point of time is in the past. In this manner, it can be ensured that the prediction is not too far directed to the future. In particular, this can be problematic in the movement of a human or animal eye due to an insufficient uniformity of the movement thereof.

According to a development, it is provided that an acceleration and/or a speed along multiple degrees of freedom are captured independently of each other and/or are evaluated independently of each other in determining the prediction data. In other words, it can be provided that the acceleration of the eye and/or of the target point along the multiple degrees of freedom is captured respectively independently of each other. For example, a respective value for the acceleration along each of the multiple degrees of freedom is independently determined. It can be provided that the speed along the multiple degrees of freedom is captured independently of each other. For example, a respective value for the speed along each of the multiple degrees of freedom can be determined independently of the remaining degrees of freedom. Alternatively or additionally, it can be provided that the acceleration and/or the speed along the multiple degrees of freedom are evaluated independently of each other in determining the prediction data. For example, it can be provided that the respective values for the acceleration and/or the speed along the individual degrees of freedom are each evaluated independently of each other for determining the prediction data or the prediction. Therein, respective partial predictions for the movement along each of the multiple degrees or freedom can be determined or created. The prediction or prediction data can then be composed of the partial predictions, for example by linear combination or addition of vectors.

A second aspect of the present invention relates to a method for controlling an eye surgical laser of a treatment apparatus during a treatment of a cornea of a human or animal eye depending on a position and/or orientation of a target point of the eye. The method according to the second aspect of the invention is based on the method according to the first aspect of the invention. Therein, the method according to the second aspect additionally includes the following method steps:

determining a position specification for a laser pulse at least depending on the prediction data, and
adjusting the laser corresponding to the position specification.

Thus, the method according to the second aspect of the invention can overall comprise the following method steps:

capturing a respective picture of the eye at least at a first point of time and a later second point of time,
determining movement information with respect to a movement of the eye and/or of the target point based on the respective pictures,
determining prediction data, which includes a prediction for a future position and/or orientation of the target point at a later point of time, based on the movement information, wherein the later point of time is temporally spaced from the second point of time by a period of time, the duration of which is at least derived from a latency of an image evaluation, in particular the steps S1 and/or S2 and/or S3,
determining a position specification for a laser pulse at least depending on the prediction data, and
adjusting the laser corresponding to the position specification.

Thus, the prediction for the future position and/or orientation of the target point is used to determine the position specification for the laser pulse. For example, the position specification for the laser pulse can be fixed in a coordinate system aligned with the eye or the cornea. In this example, the movement of the eye can conduct a relative movement between the coordinate system aligned with the eye and a world coordinate system or a coordinate system aligned with the treatment apparatus for performing the treatment. Thus, the position specification for the laser pulse can for example be determined considering the prediction data, in particular the future positions of the eye and/or of the target point, in the world coordinate system or the coordinate system aligned with the treatment apparatus. Subsequently, the laser, in particular the eye surgical laser, can be adjusted and/or oriented corresponding to the position specification. The adjustment or orientation of the eye surgical laser can for example include orienting or adjusting a beam device for beam guidance and/or beam shaping and/or beam deflection and/or beam focusing of a laser beam of the laser. For example, the future laser pulse can be oriented to the target point by correspondingly actuating the beam device according to the position specification.

According to a development, it is provided that the later point of time is temporally spaced from the second point of time by an overall period of time, wherein a duration of the overall period of time is at least derived from the latency of the image evaluation as well as from a latency for adjusting the laser. In other words, in the method for controlling the eye surgical laser, it is provided that in the overall period of time, by which the later point of time is temporally spaced from the second point of time, the latency for adjusting the laser is also considered in addition to the latency of image evaluation. Thus, the laser can be adjusted to a position specification, which considers the future position of the target point corresponding to the prediction. In this manner, a movement of the eye predicted for the overall period of time can already be considered in adjusting the laser. A more accurate adjustment of the laser can result from it.

According to a development, it is provided that a third picture of the eye is captured at a third point of time, wherein the third point of time is temporally after the second point of time, but before the later point of time, wherein in particular the prediction, which is part of the prediction data, is examined at least depending on the third picture. In other words, it can be provided that the third picture of the eye is captured at the third point of time. Therein, the third point of time is temporally between the second point of time and the later point of time. Advantageously, the prediction, which is part of the prediction data, is examined at least depending on the third picture. At this place, it is to be explicitly mentioned that the designation "third picture" does not mean that the prediction data is exclusively based on the first and the second picture. Of course, it is also possible within the scope of this development that the movement information is determined based on multiple pictures at more than two points of time and/or the prediction or the prediction data is accordingly based on respective pictures at more than two points of time. Based on the third picture, thus, the prediction, which is part of the prediction data, can be examined for its validity and its quality, respectively. The development is based on the idea that at the third point of time, at which the third picture is captured, due to the latency in adjusting the laser, it cannot be oriented or adjusted based on a position and/or orientation of the target point derived from the third picture anymore. Thus, the laser is nevertheless adjusted corresponding to the prediction or the prediction data to the position specification derived therefrom, as already previously described, despite of presence of a newer picture, namely the third picture. Therein, the third point of time is in particular between the second point of time and the later point of time such that an image evaluation of the third picture is present or determined before triggering the laser pulse. Thus, the laser previously adjusted or oriented based on the prediction, which is derived from the second picture at the second point of time among other things, cannot be adjusted with respect to the position specification anymore, but enabling or disabling the laser pulse is possible depending on the fact how good the prediction proves within the scope of the examination based on the third picture.

According to a development, it is provided that further movement information is determined depending at least on the third picture, and further prediction data, which includes a further prediction for the future position and/or orientation of the target point at the later point of time, is determined based on the further movement information. The prediction or the prediction data can be based on the second picture as the picture most current at the respective prediction point of time. The further prediction data or the further prediction can be based on the picture most current at the third point of time, namely the third picture. Thus, the further prediction data can more accurately predict the position and/or orientation of the target point at the later point of time due to the smaller period of time to be bridged by the prediction than the prediction data, which is based on the second picture at the second point of time. Examining the prediction or the prediction data can be effected based on the further prediction data or the further prediction. For example, it can be determined in the examination to what extent the prediction and the further prediction coincide or deviate from each other. At this place, it is to be again clarified that the second picture can be the respectively most current picture to adjust the laser for the laser pulse, which is to be effected at the later point of time, due to the latency both in adjusting the laser and in performing the image evaluation. Based on the further prediction data or the further prediction, adjusting the laser for the laser pulse, which is to occur at the later point of time, is no longer possible due to the overall latency. However, since only the latency of the image evaluation is significant for the examination of the prediction based on the further prediction, however, the examination is possible still before the later point of time, at which the laser is to be triggered.

According to a development, it is provided that depending on a result in examining the prediction, in particular based on the further prediction data, the laser pulse for the position specification previously adjusted based on the prediction data is enabled or a new adjustment of the laser to an updated position specification is commanded. Concretely, the laser pulse can for example be enabled exactly if a deviation between the prediction and the further prediction or between the prediction data and the further prediction data is less than a predetermined threshold value. Analogously, the new adjustment of the laser to the updated position specification can be commanded if the previously mentioned deviation is greater than the predetermined threshold value. As already above described, the position specification is derived from the prediction for the position and/or orientation of the target point at the later point of time. If the threshold value is exceeded by the above mentioned deviation, the updated position specification can be determined. In addition, the laser can be adjusted or oriented corresponding to the updated position specification.

The updated position specification can for example be effected based on a prediction for the future position and/or orientation of the target point at a still later point of time, which is temporally after the later point of time. This prediction of the position and/or orientation of the target point for the still later point of time can be effected analogously to the prediction for the future position and/or orientation of the target point at the later point of time. In this case, analogous movement information with respect to the movement of the eye and/or of the target point can be determined at least based on the second and the third picture. The prediction for the still later point of time can then be determined based on the movement information, which has been determined from the second and the third picture.

However, due to the analogy for determining the prediction for the future position and/or orientation of the target point at the later point of time, this is not set forth in repeating manner at this place.

According to a development, it is provided that
- a fourth picture of the eye is captured at least approximately at the later point of time, an actual position and/or orientation of the target point at the later point of time is determined based on the fourth picture,
- the actual position of the eye at the later point of time is compared to the prediction, which is part of the prediction data, and/or to the further prediction, which is part of the further prediction data, and
- depending on a result of the respective comparison, a first algorithm for determining the prediction data and/or a second algorithm for determining the further prediction data are changed.

If the respective pictures, thus, for example the first, the second, the third and/or the fourth picture, are part of a video signal, exactly that frame of the video signal can be selected as the fourth picture, the capturing time of which is closest to the later point of time. Thus, the fourth picture relates to the eye approximately at the later point of time. In other words, the fourth picture images the eye approximately at the later point of time. Thus, it can be determined based on the fourth picture, which position and/or orientation the target point actually had at the later point of time. By comparing the actual position of the eye at the later point of time to the prediction (which is part of the prediction data) for the position of the eye at the later point of time, it can be determined or ascertained how good this prediction was. For example, a quality of the prediction can be evaluated and quantified, respectively, by a value, which indicates the deviation between actual and predicted position. By comparing the actual position of the eye at the third point of time to the further prediction (which is part of the further prediction data) for the position of the eye at the later point of time, it can be determined or ascertained how good this further prediction was. For example, a quality of the further prediction can be evaluated and quantified, respectively, by a value, which indicates the deviation between actual and predicted position.

Depending on the deviation between actual position of the eye and the prediction, the first algorithm, which is used for determining the prediction or prediction data, can be changed, that is trained, refined or adapted. In this manner, the quality of the first algorithm is refined or improved for future predictions. Depending on the deviation between actual position of the eye and the further prediction, the second algorithm, which is used for determining the further prediction or further prediction data, can be changed, that is trained, refined or adapted. In this manner, the quality of the second algorithm is refined or improved for future further predictions.

A third aspect of the present invention relates to a control device, which is configured to perform one of the above described methods. The above cited advantages result. For example, the control device can be configured as a control chip, control appliance or application program ("app"). The control device can preferably comprise a processor device and/or a data storage. An appliance or an appliance component for electronic data processing is understood by a processor device. For example, the processor device can comprise at least one microcontroller and/or at least one microprocessor. Preferably, a program code for performing the method according to the invention can be stored on the optional data storage. The program code can then be adapted, upon execution by the processor device, to cause the control device to perform one of the above described embodiments of one or both methods according to the invention.

A fourth aspect of the present invention relates to a treatment apparatus with at least one eye surgical laser for the separation of a tissue predefined by the control data, in particular of a corneal volume with predefined interfaces of a human or animal eye by means of photodisruption and/or photoablation, and at least one control device for the laser or lasers, which is formed to execute the steps of the method according to the first and/or the second aspect of the invention. The treatment apparatus according to the invention allows that the disadvantages occurring in the use of usual ablative and/or photodisruptive treatment apparatuses are reliably reduced or even avoided.

In a further advantageous configuration of the treatment apparatus according to the invention, the laser can be suitable to emit laser pulses in a wavelength range between 300 nm and 1400 nm, preferably between 700 nm and 1200 nm, at a respective pulse duration between 1 fs and 1 ns, preferably between 10 fs and 10 ps, and a repetition frequency of greater than 10 kilohertz (kHz), preferably between 100 kHz and 100 megahertz (MHz). Such a femtosecond laser is particularly well suitable for removing tissue within the cornea. The use of photodisruptive and/or photoablative lasers in the method according to the invention additionally has the advantage that the irradiation of the cornea does not have to be effected in a wavelength range below 300 nm. This range is subsumed by the term "deep ultraviolet" in the laser technology. Thereby, it is advantageously avoided that an unintended damage to the cornea is effected by these very short-wavelength and high-energy beams. Photodisruptive lasers of the type used here usually input pulsed laser radiation with a pulse duration between 1 fs and 1 ns into the corneal tissue. Thereby, the power density of the respective laser pulse required for the optical breakthrough can be spatially narrowly limited such that a high incision accuracy in the generation of the interfaces is allowed. In particular, the range between 700 nm and 780 nm can also be selected as the wavelength range.

In further advantageous configurations of the treatment apparatus according to the invention, the control device can comprise at least one storage device for at least temporary storage of at least one control dataset, wherein the dataset or datasets include(s) control data for positioning and/or for focusing individual laser pulses in the cornea; and can comprise at least one beam device for beam guidance and/or beam shaping and/or beam deflection and/or beam focusing of a laser beam of the laser. Therein, the mentioned control dataset includes the control data determined in the method for removing the tissue.

Further features and the advantages thereof can be taken from the descriptions of the first inventive aspect, wherein advantageous configurations of each inventive aspect are to be regarded as advantageous configurations of the respectively other inventive aspect.

A fifth aspect of the invention relates to a computer program including commands, which cause the treatment apparatus according to the fourth inventive aspect to execute the method steps according to the first inventive aspect and/or the method steps according to the second inventive aspect.

A sixth aspect of the invention relates to a computer-readable medium, on which the computer program according to the fifth inventive aspect is stored. Further features and the advantages thereof can be taken from the descriptions of the first to fifth inventive aspects, wherein advantageous configurations of each inventive aspect are to be regarded as advantageous configurations of the respectively other inventive aspect.

BRIEF DESCRIPTION OF DRAWINGS

Further features are apparent from the claims, the figures and the description of figures. The features and feature combinations mentioned above in the description as well as the features and feature combinations mentioned below in the description of figures and/or shown in the figures alone are usable not only in the respectively specified combination, but also in other combinations without departing from the scope of the invention. Thus, implementations are also to be considered as encompassed and disclosed by the invention, which are not explicitly shown in the figures and explained, but arise from and can be generated by separated feature combinations from the explained implementations. Implementations and feature combinations are also to be considered as disclosed, which thus do not comprise all of the features of an originally formulated independent claim. Moreover, implementations and feature combinations are to be considered as disclosed, in particular by the implementations set out above, which extend beyond or deviate from the feature combinations set out in the relations of the claims.

DETAILED DESCRIPTION

Figure 1:
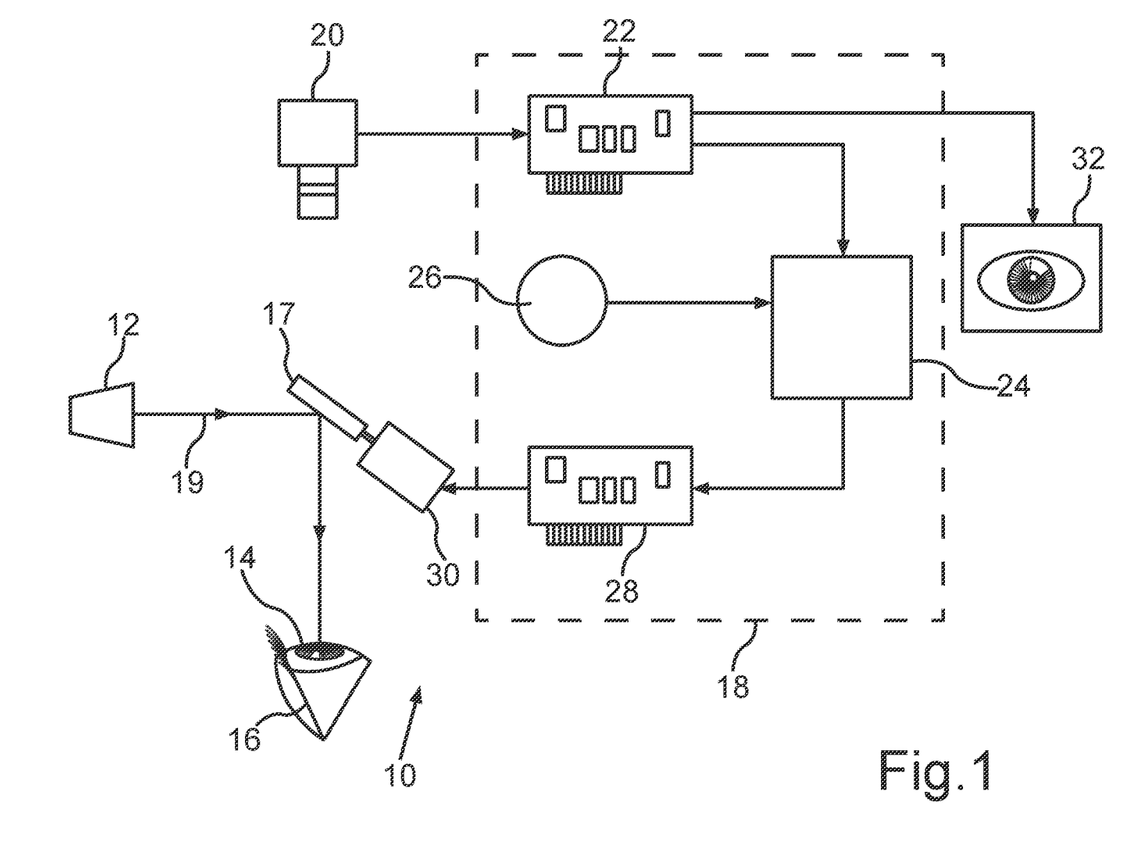
FIG. 1 is a schematic representation of a treatment apparatus according to the invention according to an exemplary embodiment.

FIG. 1 shows a schematic representation of a treatment apparatus 10 with an eye surgical laser 12 for removing a tissue 14 of a human or animal eye 16 by means of photodisruption and/or photoablation. For example, the tissue 14 can represent a lenticule or also volume body, which can be separated from a cornea of the eye 16 by the eye surgical laser 12 for correcting a visual disorder. A geometry of the tissue 14 to be removed, thus a tissue removal geometry 14, can be provided by a control device 18, in particular in the form of control data, such that the laser 12 emits pulsed laser pulses in a pattern predefined by the control data into the cornea of the eye 16 to remove the tissue 14. Alternatively, the control device 18 can be a control device 18 external with respect to the treatment apparatus 10.

Furthermore, FIG. 1 shows that the laser beam 19 generated by the laser 12 can be deflected towards the eye 16 by means of a beam deflection device 22, namely a beam deflection apparatus such as for example a rotation scanner, to remove the tissue 14. The beam deflection apparatus 22 can also be controlled by the control device 18 to remove the tissue 14.

Preferably, the illustrated laser 12 can be a photodisruptive and/or photoablative laser, which is formed to emit laser pulses in a wavelength range between 300 nanometers and 1400 nanometers, preferably between 700 nanometers and 1200 nanometers, at a respective pulse duration between 1 femtosecond and 1 nanosecond, preferably between 10 femtoseconds and 10 picoseconds, and a repetition frequency of greater than 10 kilohertz, preferably between 100 kilohertz and 100 megahertz. Optionally, the control device 18 additionally comprises a storage device (not illustrated) for at least temporary storage of at least one control dataset, wherein the control dataset or datasets include(s) control data for positioning and/or for focusing individual laser pulses in the cornea. The position data of the individual laser pulses is ascertained at least based on the method described below.

Figure 2:
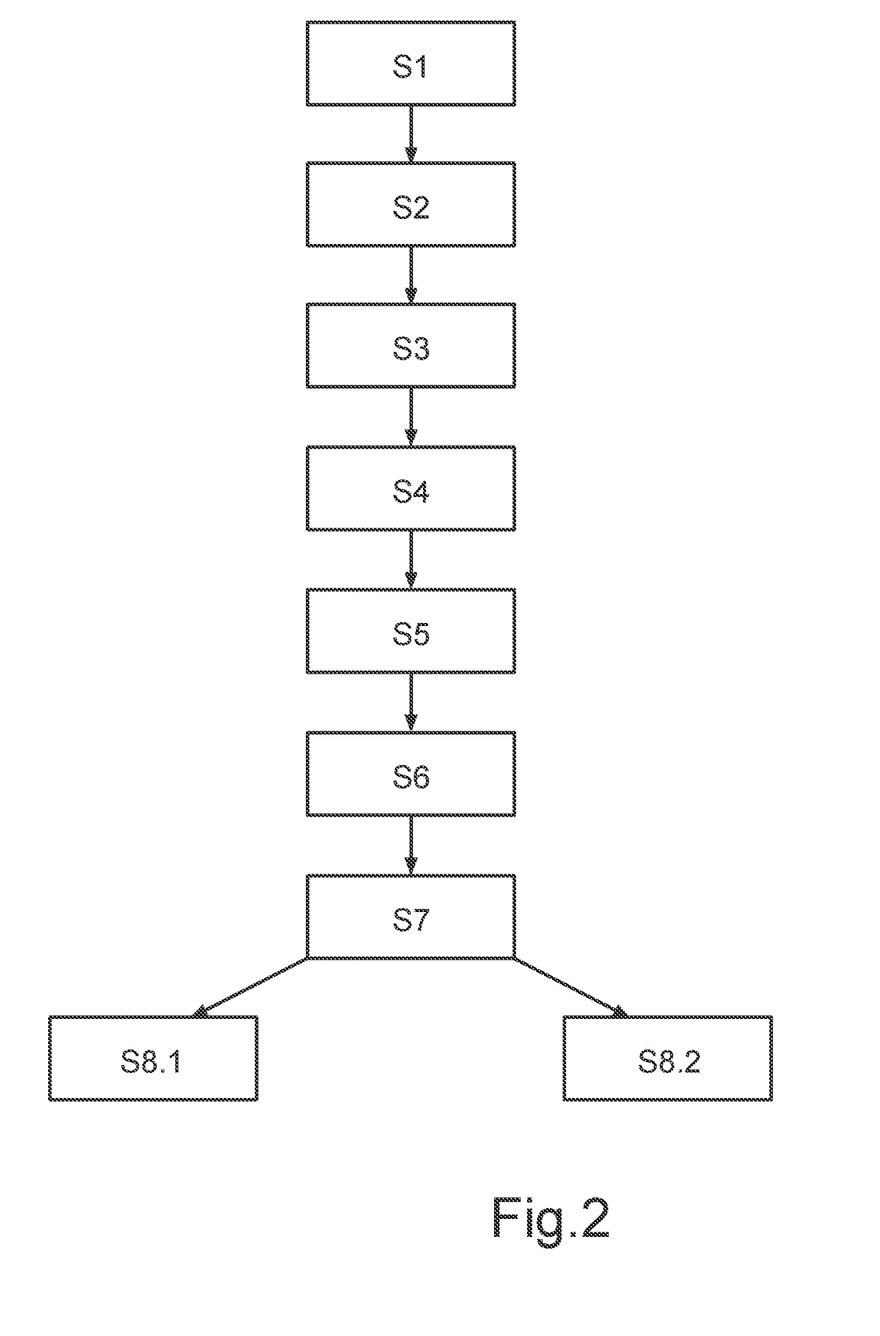
FIG. 2 is a flow diagram of a method according to the invention according to an exemplary embodiment.

FIG. 2 shows a flow diagram of an exemplary embodiment of a method for controlling the eye surgical laser 12 of the treatment apparatus 10 during a treatment of a cornea of the human or animal eye 16 depending on a position and/or orientation of a target point of the eye 16. Therein, the laser beam of the laser 12 or laser pulses of the laser 12 is or are to meet the target point of the eye 16 as accurately as possible. Since the eye 16 is often in motion and complete "immobilization" is not completely possible, the movements of the eye 16 are to be captured and are considered, thus compensated for, in beam guidance of the laser beam 19 of the laser 12 or the laser pulses of the laser 12. Thus, the method serves for adapting the predetermined laser pulses with respect to their respective positioning or orientation such that the movement of the eye 16 is compensated for.

For determining the movement or the "tracking" of the eye 16 and/or of the target point, the treatment apparatus 10 comprises at least one camera 20. The control device 18 is formed to evaluate images of the eye 16. The camera 20 can be formed to capture these images of the eye 16 and to communicate them to the control device 18. The control device 18 can be formed to receive images of the eye 16 from the camera 20. In particular, the images from the camera 20 are a video signal, which is composed of a plurality of consecutive frames. Depending on the image capturing rate of the camera 20, for instance 1200 Hz or 1200 fps (frames per second), a latency of the camera 20 can be slightly below one millisecond.

The control device 18 can comprise an image processing unit 22. The images of the eye 16 can each be processed and/or evaluated by the image processing unit 22. In particular, the position of the eye 16 and/or of the target point can respectively be determined by the image processing unit 22. The image processing unit 22 can for example include a microprocessor, a digital signal processor, an FPGA or the like. Herein, a latency of about 1 ms, for example 0.9 ms, can arise. The processed image can further be output to an output unit 32, for instance a screen.

By a main control unit 24 of the control device 18, the results of capturing the position and/or movement of the eye 16 can be correlated with the predetermined laser pulses from a pulse list 26. Here, it can be determined, corresponding to which position specification the laser 12 or the beam device 17 has to be adjusted to guide a laser pulse assigned by the pulse list 26 to the target position. Coordinates for the position specification of the laser 12 can be composed of coordinates of a respective laser pulse as well as an offset, wherein the coordinates can be assigned by the pulse list 26 and/or the offset results from the position and/or movement of the eye 16 or of the target point. Therein, the offset serves for compensating for the movement of the eye. Herein, the latency is for example about 90 µs. Corresponding to the position specification, the laser 12 or the beam device 17 can then be adjusted or oriented. This can be effected by an actuation unit 28. The latency in the actuation of the actuation unit 28 is exemplarily about 100 ns. For example, the actuation unit 28 can be provided by an amplifier for actuating the beam device 17. The actuation unit 28 can for example actuate or supply an adjusting unit 30 with a signal, a current or a voltage. The adjusting unit 30 is in particular formed for mechanically orienting the beam device 17 corresponding to the actuation by the actuation unit 28. A latency for adjusting or orienting the beam device 17 can for example be up to 1 ms, for example, this is depending on an adjusting path in orienting. The main control unit 24 can for example include a microprocessor, a digital signal processor, an FPGA or the like.

By the following steps of the present embodiment of the method, the mentioned latencies are compensated for:

In a step S1, capturing a respective picture of the eye at least at a first point of time and at a later second point of time is effected. This can be effected by the camera 20 as already above described. Alternatively or additionally, capturing the images can be performed by the control unit 18 in that it receives the images from the camera 20. For example, the camera 20 captures at least a first picture at the first point of time and a second picture at the later second point of time. Of course, multiple frames of a video signal each captured one after the other can also be captured and used for the further method.

In a step S2, determining movement information with respect to a movement of the eye and/or of the target point is effected based on the respective pictures. In particular, this can be performed by the control unit 18. In particular, the movement information is determined by the image processing unit 22. Hereto, the image processing unit 22 can in particular evaluate the first and the second picture. For example, a relative movement of the eye and/or of the target point between the first and the second picture can be determined as the movement information. In case of multiple pictures, a respective relative movement between respective pictures can be determined as a part of the movement information. For example, the respective relative movement between two images captured at adjacent points of time can be captured or determined. The movement information or the relative movement can for example be determined and indicated, respectively, in the form of a respective vector (in case of a translational movement) and/or an angle (in case of a rotational movement). Therein, the movement information for different degrees of freedom, for instance for three independent translational degrees of freedom and/or three independent rotational degrees of freedom, can be determined in common and/or independently of each other.

In a step S3, determining prediction data, which includes a prediction for a future position and/or orientation of the target point at a later point of time, is effected. Determining the prediction data is effected based on the movement information. Therein, the later point of time is preferably temporally spaced from the second point of time by a period of time, the duration of which is at least derived from an overall latency of the image evaluation and adjustment of the laser 12 or the beam device 17. Based on the movement information, thus, the prediction for the future position and/or orientation of the target point at the later point of time can be determined. This prediction can be determined as a part of the prediction data. Therein, the later point of time is temporally spaced from the second point of time by the period of time, the duration of which is at least derived from the overall latency of the image evaluation and the adjustment of the laser 12 or the beam device 17. For example, the overall latency results by the added latencies of the steps S1, S2, S3, S4 and S5. Thus, the overall latency can result by addition of the respective latencies of the camera 20 (about 1 ms), the image processing unit 22 (about 0.9 ms), the main control unit 24 (about 90 µs), the actuation unit 28 (about 100 ns) and the orientation of the beam device 17 (about 1 ms). This overall latency can be preset by a preset average value. Alternatively, the respective latencies can be preset by a respective average value. The step S3 can for example be performed by the image processing unit 22.

In a step S4, determining the position specification for the laser pulse is effected at least depending on the prediction data. Thus, the prediction for the future position and/or orientation of the target point is used to determine the position specification for the laser pulse. For example, the position specification for the laser pulse can be fixed in a coordinate system aligned with the eye 16 or the cornea 14 by the pulse list 26. In this example, the movement of the eye 16 can conduct a relative movement between the coordinate system aligned with the eye 16 and a world coordinate system or a coordinate system aligned with a treatment apparatus 10. Thus, the position specification for the laser pulse can for example be determined considering the prediction data, in particular the future positions of the eye 16 and/or of the target point, in the world coordinate system or the coordinate system aligned with the treatment apparatus.

In a step S5, adjusting the laser 12 corresponding to the position specification is effected. Thus, the laser 12 can be adjusted and/or oriented corresponding to the position specification. Adjusting or orienting the laser 12 is presently effected by orienting or adjusting the beam device 17 for beam guidance and/or beam shaping and/or beam deflection and/or beam focusing of the laser beam 19 of the laser 12. For example, the future laser pulse can be oriented to the target point by correspondingly actuating the beam device 17 according to the position specification.

In a step S6, further movement information is determined depending on at least one third picture. Hereto, a third picture of the eye 16 is in particular captured at a third point of time, wherein the third point of time is temporally after the second point of time, but before the later point of time. The third picture can be a frame of the video signal of the camera 20 following the second picture. In the step S6, the prediction, which is part of the prediction data, is in particular examined at least depending on the third picture. In other words, it can be provided that the third picture of the eye is captured at the third point of time. Therein, the third point of time is temporally between the second point of time and the later point of time. Based on the third picture, the prediction, which is part of the prediction data, can thus be examined for its validity and its quality, respectively. This is based on the idea that at the third point of time, at which the third picture is captured, due to the latency in adjusting the laser, it cannot be oriented or adjusted based on a position and/or orientation of the target point derived from the third picture anymore. Thus, the laser is nevertheless adjusted corresponding to the prediction or the prediction data to the position specification derived therefrom, as already described above, despite of presence of a newer picture, namely the third picture. Therein, the third point of time is in particular between the second point of time and the later point of time such that an image evaluation of the third picture is present or determined before triggering the laser pulse. Thus, the laser previously adjusted or oriented based on the prediction, which is derived from the second picture at the second point of time among other things, can no longer be adjusted with respect to the position specification, but enabling or disabling the laser pulse is possible depending on the fact, how good the prediction proves within the scope of the examination based on the third picture.

As a part of step S6, it is presently provided that the further movement information is determined depending on at least the third picture. In a following step S7, at least based on the third picture or based on the further movement information, further prediction data, which includes a further prediction for the future position and/or orientation of the target point at the later point of time, is determined. The prediction or the prediction data can be based on the second picture as the picture most current at the respective prediction point of time. The further prediction data or the further prediction can be based on the picture most current at the third point of time, namely the third picture. Thus, the further prediction data can more accurately predict the position and/or orientation of the target point at the later point of time due to the smaller period of time to be bridged by the prediction than the prediction data, which is based on the second picture at the second point of time.

Depending on a result in examining the prediction, based on the further prediction data, the laser pulse can be enabled (step 8.1) for the position specification previously adjusted based on the prediction data or a new adjustment of the laser 12 to an updated position specification can be commanded (step 8.2). The examination of the prediction or the prediction data can be effected based on the further prediction data or the further prediction. In the examination, it can for example be determined to what extent the prediction and the further prediction coincide or deviate from each other. Concretely, the laser pulse can for example be enabled exactly if a deviation between the prediction and the further prediction or between the prediction data and the further prediction data is less than a predetermined threshold value. Analogously, the new adjustment of the laser 12 or of the beam device 17 to the updated position specification can be commanded if the previously mentioned deviation is greater than the predetermined threshold value. As already above described, the position specification is derived from the prediction for the position and/or orientation of the target point at the later point of time. If the threshold value is exceeded by the above mentioned deviation, the updated position specification can be determined. In addition, the laser can be adjusted or oriented corresponding to the updated position specification. At this place, it is to be again clarified that the second picture can be the respectively most current picture to adjust the laser for the laser pulse, which is to be effected at the later point of time, due to the latency both in adjusting the laser 12 and in performing the image evaluation. Based on the further prediction data or the further prediction, adjustment of the laser 12 for the laser pulse, which is to occur at the later point of time, is not possible anymore due to the overall latency. However, since only the latency of the image evaluation is significant for examining the prediction based on the further prediction, however, the examination is possible still before the later point of time, at which the laser is to be triggered.

Figure 3:
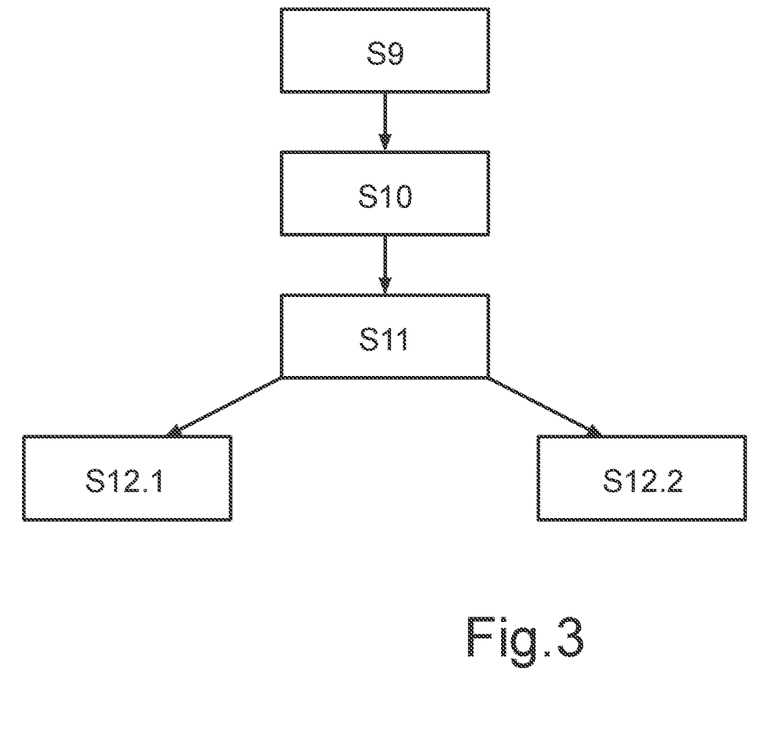
FIG. 3 is a flow diagram of further steps of the method according to the invention according to the exemplary embodiment.

FIG. 3 shows further, optional method steps of the method in a further flow diagram. They can be performed subsequent to the method according to FIG. 2.

A step S9 provides that a fourth picture of the eye 16 is captured at least approximately at the later point of time. A step S10 provides that an actual position and/or orientation of the target point at the later point of time is determined based on the fourth picture. A step S11 provides that the actual position of the eye 16 at the later point of time is compared to the prediction, which is part of the prediction data, and/or to the further prediction, which is part of the further prediction data. A step S12.1 provides that a first algorithm for determining the prediction data is changed depending on a result of the comparison. A step S12.2 provides that a second algorithm for determining the further prediction data is changed depending on a result of the comparison.

If the respective pictures, thus, for example the first, the second, the third and/or the fourth picture, are part of a video signal, exactly that frame of the video signal can be selected as the fourth picture, the capturing time of which is closest to the later point of time. Thus, the fourth picture relates to the eye approximately at the later point of time. In other words, the fourth picture images the eye approximately at the later point of time. Thus, it can be determined based on the fourth picture, which position and/or orientation the target point actually had at the later point of time. By comparing the actual position of the eye at the later point of time to the prediction (which is part of the prediction data) for the position of the eye at the later point of time, it can be determined or ascertained, how good this prediction was. For example, a quality of the prediction can be evaluated and quantified, respectively, by a value, which indicates the deviation between actual and predicted position. By comparing the actual position of the eye at the third point of time to the further prediction (which is part of the further prediction data) for the position of the eye at the later point of time, it can be determined or ascertained how good this further prediction was. For example, a quality of the further prediction can be evaluated and quantified, respectively, by a value, which indicates the deviation between actual and predicted position.

Depending on the deviation between actual position of the eye and the prediction, the first algorithm, which is used for determining the prediction or prediction data, can be changed, that is trained, refined or adapted. In this manner, the quality of the first algorithm is refined or improved for future predictions. Depending on the deviation between actual position of the eye and the further prediction, the second algorithm, which is used for determining the further prediction or further prediction data, can be changed, that is trained, refined or adapted. In this manner, the quality of the second algorithm is refined or improved for future further predictions.

LIST OF REFERENCE CHARACTERS

10 Treatment apparatus
12 laser
14 tissue
16 eye
17 beam deflection device
18 control device
19 laser beam
20 camera
22 image processing unit
24 main control unit
26 pulse list
28 actuation unit
30 adjusting unit
32 output unit
S1 to 8.2 method steps
S9 to S12.2 method steps

What is claimed is:

1. A method for controlling an eye surgical laser of a treatment apparatus during a treatment of a cornea of a human or animal eye depending on a position and/or orientation of a target point of the human or animal eye, wherein the method comprises the following steps:

capturing respective pictures of the human or animal eye at least at a first point of time and at a second point of time;

determining movement information with respect to a movement of the human or animal eye and/or of the target point based on the respective pictures;

determining prediction data, which includes a prediction for a future position and/or orientation of the target point at a later point of time, based on the movement information, wherein the later point of time is temporally spaced from the second point of time by a period of time, the duration of which is at least derived from a latency of an image evaluation;

determining a position specification for a laser pulse at least depending on the prediction data, and adjusting the eye surgical laser corresponding to the position specification;

wherein a third picture of the human or animal eye is captured at a third point of time, wherein the third point of time is temporally after the second point of time, but before the later point of time, wherein the prediction, which is part of the prediction data, is examined at least depending on the third picture; and depending on a result in the examination of the prediction, the laser pulse for the position specification previously adjusted based on the prediction data is enabled, or a new adjustment of the eye surgical laser to an updated position specification is commanded.

2. The method according to claim 1, wherein the later point of time is temporally spaced from the second point of time by an overall period of time, wherein a duration of the overall period of time is at least derived from the latency of an image evaluation as well as a latency for adjusting the eye surgical laser.

3. The method according to claim 1, wherein further movement information is determined depending on at least the third picture, and based on the further movement information, further prediction data, which includes a further prediction for the future position and/or orientation of the target point at the later point of time, is determined.

4. The method according to claim 1, wherein a fourth picture of the human or animal eye is captured at least approximately at the later point of time, based on the fourth picture, an actual position and/or orientation of the target point at the later point of time are determined, and the actual position of the human or animal eye at the later point of time is compared to the prediction, which is part of the prediction data, and/or to a further prediction, which is part of further prediction data, depending on a result of the comparison, a first algorithm for determining the prediction data and/or a second algorithm for determining the further prediction data are changed.

5. The method according to claim 1, wherein during determining of the prediction data, the later point of time is temporally spaced at most as far as the first point of time.

6. The method according to claim 1, wherein an acceleration and/or a speed along multiple degrees of freedom are captured independently of each other and/or are evaluated independently of each other in determining the prediction data.

7. A control device, which is formed to cause a treatment apparatus to perform a method according to claim 1.

8. A treatment apparatus with at least one eye surgical laser for performing a cornea correction on a cornea by means of photodisruption and/or photoablation and with a control device according to claim 7.

9. The treatment apparatus according to claim 8, wherein the eye surgical laser is formed to emit laser pulses in a wavelength range between 300 nm and 1400 nm, at a respective pulse duration between 1 fs and 1 ns, and a repetition frequency of greater than 10 KHz.

10. The treatment apparatus according to claim 8, wherein the control device comprises at least one storage device for at least temporary storage of at least one control dataset, wherein the at least one control dataset or datasets include(s) control data for positioning and/or focusing individual laser pulses in the cornea; and includes at least one beam device for beam guidance and/or beam shaping and/or beam deflection and/or beam focusing of a laser beam of the eye surgical laser.

11. A non-transitory computer-readable medium having a computer program stored thereon, the computer program including commands which cause a treatment apparatus with at least one eye surgical laser for performing a cornea correction on a cornea by means of photodisruption and/or photoablation and with a control device, to execute a method according to claim 1.

12. A control device, which is formed to cause a treatment apparatus to perform a method according to claim 1.

13. A treatment apparatus with at least one eye surgical laser for performing a cornea correction on a cornea by means of photodisruption and/or photoablation and with a control device according to claim 12.

* * * * *